US 7,978,892 B2

(12) United States Patent
Quadling et al.

(10) Patent No.: US 7,978,892 B2
(45) Date of Patent: Jul. 12, 2011

(54) 3D PHOTOGRAMMETRY USING PROJECTED PATTERNS

(75) Inventors: Mark S. Quadling, Plano, TX (US);
Henley S. Quadling, Dallas, TX (US);
Ye Li, Plano, TX (US); Andrei Tchouprakov, Plano, TX (US)

(73) Assignee: D4D Technologies, LLC, Richardson, TX (US)

( * ) Notice: Subject to any disclaimer, the term of this patent is extended or adjusted under 35 U.S.C. 154(b) by 930 days.

(21) Appl. No.: 11/923,297

(22) Filed: Oct. 24, 2007

(65) Prior Publication Data
US 2008/0101688 A1 May 1, 2008

Related U.S. Application Data

(60) Provisional application No. 60/854,336, filed on Oct. 25, 2006, provisional application No. 60/888,878, filed on Feb. 8, 2007.

(51) Int. Cl.
*G06K 9/00* (2006.01)
*A61B 6/00* (2006.01)

(52) U.S. Cl. .................. 382/128; 382/154; 600/476

(58) Field of Classification Search .............. 382/100, 382/106, 108, 128, 129, 130, 131, 132, 133, 382/134, 154, 168, 173, 181, 199–203, 216, 382/232, 254, 276, 285, 291, 305, 312; 356/601; 433/24; 600/476

See application file for complete search history.

(56) References Cited

U.S. PATENT DOCUMENTS

| 6,668,082 B1* | 12/2003 | Davison et al. ............... 382/190 |
| 6,751,344 B1* | 6/2004 | Grumbine ...................... 382/154 |
| 7,585,172 B2* | 9/2009 | Rubbert et al. .................. 433/24 |
| 2001/0016063 A1* | 8/2001 | Albeck et al. ................. 382/154 |
| 2004/0105580 A1* | 6/2004 | Hager et al. ................... 382/154 |
| 2004/0201856 A1* | 10/2004 | Quadling et al. ............. 356/601 |
| 2004/0254476 A1* | 12/2004 | Quadling et al. ............. 600/476 |
| 2005/0271264 A1 | 12/2005 | Ito et al. |
| 2008/0013943 A1 | 1/2008 | Rohaly |

OTHER PUBLICATIONS

Patent Cooperation Treaty, International Search Report and Written Opinion of the International Searching Authority from International Patent Application No. PCT/US2007/082468, dated May 9, 2008, 9 pages.

* cited by examiner

*Primary Examiner* — Seyed Azarian
(74) *Attorney, Agent, or Firm* — Haynes and Boone, LLP

(57) ABSTRACT

A structured light pattern digitizing method is combined with photogrammetry to determine a 3D model of an object. The structured light digitizing operation generates a 3D model of the object being scanned, and this model is then used to compute a higher accuracy model using photogrammetry.

12 Claims, 3 Drawing Sheets

Figure 1

3D PHOTOGRAMMETRY USING PROJECTED PATTERNS

This application is based on and claims priority from Ser. No. 60/854,336, filed Oct. 25, 2006, and Ser. No. 60/888,878, filed Feb. 8, 2007.

BACKGROUND OF THE INVENTION

1. Technical Field

This disclosure relates generally to techniques for obtaining a three-dimensional (3D) model of an object, such as a dental item.

2. Background of the Related Art

Photogrammetry is a remote sensing technique in which geometric properties about an object are determined from photographic images. In a typical application, two or more photographs or images of the object are taken from different positions. By matching features between the two images, it is then possible to determine very accurately the 3D coordinates for each matched feature.

Although photogrammetry is a well-developed art, the matching of pixels can be very difficult when dealing with a surface area of the object that has few features. Moreover, the pixel matching algorithms are computationally expensive. As a consequence photogrammetry has not been adapted for dental imaging applications.

BRIEF SUMMARY OF THE INVENTION

In a representative method, the use of a structured light pattern digitizing method is combined with photogrammetry to determine a 3D model of an object. The structured light digitizing operation generates a 3D model of the object being scanned, and this model is then used to compute a higher accuracy model using photogrammetry. Unlike other methods using photogrammetry, the disclosed technique obviates a computationally expensive matching of pixels between different images. It has the added advantage of further providing detail in areas where photogrammetry normally is unable to provide data, e.g., due to the surface being unusually feature free in that particular area.

The foregoing has outlined some of the more pertinent features of the invention. These features should be construed to be merely illustrative. Many other beneficial results can be attained by applying the disclosed invention in a different manner or by modifying the invention as will be described.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION OF AN ILLUSTRATIVE EMBODIMENT

A dental imaging technique uses a structured light pattern digitizing method combined with photogrammetry to determine a 3D model of an object, such as a dental item. The dental item may be any of: a preparation, an implant, an abutment, a bridge, an orthodontic appliance, an oral appliance, and other physical dental items. The structured light pattern digitizing method may be performed using an intra-oral digitizer, such as the E4D Dentist system of D4D Technologies, Richardson, Tex., and described by U.S. Pat. No. 7,184,150. The disclosures of these patents are incorporated herein by reference. In system of this type, a prepared area and adjacent teeth are scanned using the digitizer, and a 3D model of the prepared area is obtained. A patient may also be instructed to bite on a bite strip, and the bite strip subsequently scanned to obtain an opposing dentition model. This information may then be used to produce a 3D model of a desired restoration. Such a process can be performed using a computer-aided design system. Of course, the present invention is not limited for use with such techniques and systems.

Figure 1:
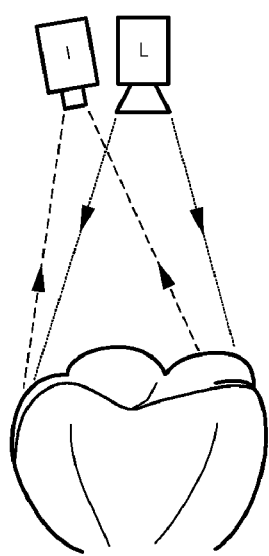
FIG. 1 illustrates how a digitizer is oriented relative to an object that is desired to be scanned in 3D to obtain a point cloud of 3D coordinates on the surface of the object.
Figure 2:
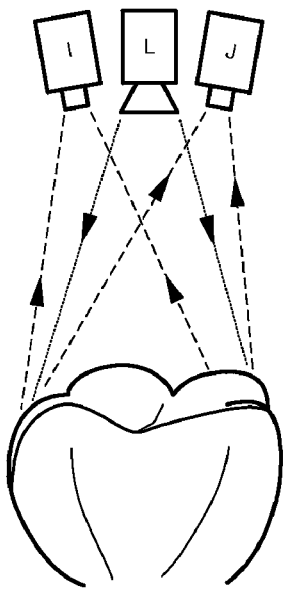
FIG. 2 illustrates an alternate embodiment, where the digitizer includes a projection portion and a pair of imaging portions.

In one aspect of the method of this disclosure, a digitizer is oriented relative to an object that is desired to be scanned in 3D to obtain a point cloud of 3D coordinates on the surface of the object. Referring to FIG. 1, the digitizer comprises a projection portion L and an imaging portion I. Referring to FIG. 2, in an alternate embodiment, the digitizer may also comprise a projection portion L and two imaging portions I and J (see also FIG. 6, described below). Indeed, in general, there is no limit to the number of imaging portions that may be included in the system. The projection portion projects a pattern onto the object using light, where the pattern may range from a single point to full illumination, or any variation in between these two extremes. For example, the pattern may be a series of segments, as described in U.S. Pat. Nos. 7,142,312 and 7,184,150. The pattern may also comprise complete illumination as well, for example, where the number of segments is so large that they effectively coalesce. The one or more imaging portions observe the projected pattern on the object, and deduce the 3D information on the object, preferably using triangulation techniques as described in the above-identified patents. In the case where there are two imaging portions, both may be used to generate the 3D data, in which case the 3D data is then that given by all 3D points generated by each of the two imaging portions.

Figure 3:
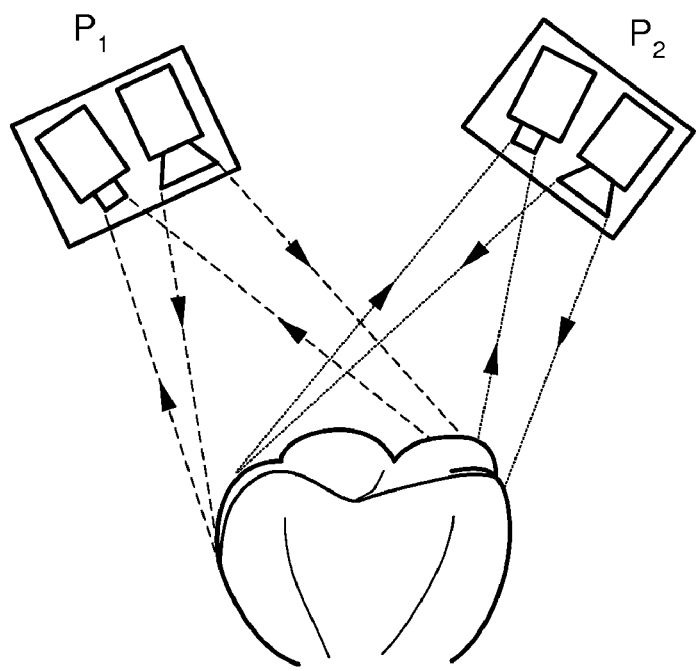
FIG. 3 illustrates the digitizer of FIG. 1 oriented in different positions relative to the object that is desired to be scanned.
Figure 4:
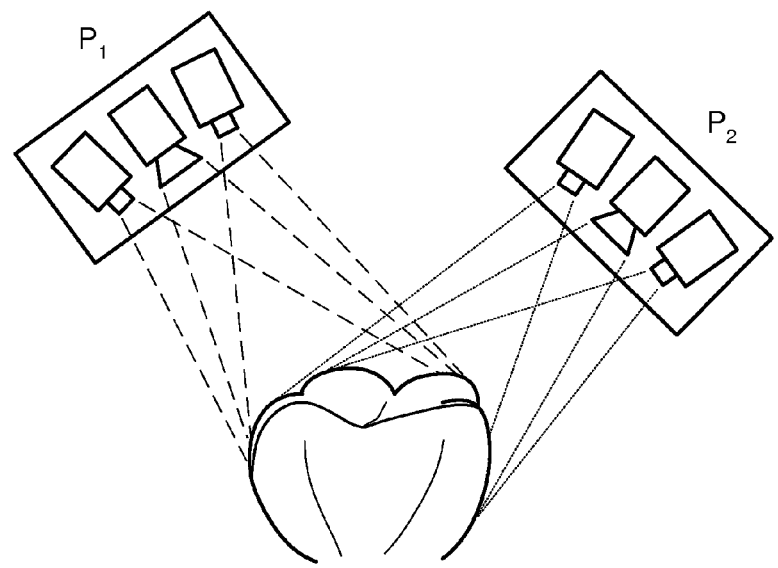
FIG. 4 illustrates the digitizer of FIG. 2 oriented in different positions relative to the object.

In the following description, assume that the above-described configuration is assembled into a digitizer (or, more generally, an imaging system) that may be oriented in different positions relative to the object that is desired to be scanned. Referring to FIG. 3 and FIG. 4, the digitizer may then be positioned relative to the object in different positions. In particular, FIG. 3 corresponds to the digitizer of FIG. 1, where the digitizer includes a projection portion and a single imaging portion. FIG. 4 corresponds to the digitizer of FIG. 2, where the digitizer includes a projection portion and a pair of imaging portions. In each of these figures, the digitizer is positioned in at least two (2) different (first and second) positions relative to the object. This is not a limitation, however. Moreover, assume that there are N such positions. As used herein, the letter M is used to refer to one of these positions, so that M varies between 1 and N.

Obtaining an Estimate for the 3D Data

At a position M, the digitizer projects a series of patterns using the method described, for example, in U.S. Pat. No. 7,142,312 or U.S. Pat. No. 7,184,150. A pattern typically comprises a plurality of curves, with each curve being substantially parallel to one another. The patterns are imaged by the imaging portion (FIG. 1) or imaging portions (FIG. 2); using the known methods disclosed in those patents, the system determines a 3D data set in the coordinate space of the digitizer for that object being scanned. If there are two imaging portions, each may be paired with the projection portion, and each may generate 3D data separately. The process of scanning then follows by repositioning the digitizer to repeat the same process from another location, preferably for each position M going from 1 through N. FIG. 3 shows two such locations, as does FIG. 4. Each position results in one or two (in the case of a two imaging portion system) sets of 3D coordinates, each one in the coordinate space of the digitizer at that particular location. At each position M, preferably an additional image with full (or substantially full) illumination of the object is also taken. In the case of a single image portion digitizer, for each position M, the result is a point cloud $C_M$ of 3D coordinates, and an image $I_M$. In the case of a double image portion digitizer, the result is a point cloud $C_M^L$ of 3D coordinates and an image $I_M^L$ associated with one of the imaging units, and another point cloud $C_M^R$ and image $I_M^R$ associated with the other imaging unit. These images are used in a subsequent step for the photogrammetry computation, as will be seen.

For each position $M_1$ of the digitizer, it can be assumed that there is at least one other position $M_2$ where the field of views overlap, so that the respective images and point clouds share at least some portion in common. In the description that follows, assume that, in fact, each new position following the first has this overlap with at least the immediately preceding position. It will be apparent to one of ordinary skill, however, that the description that follows can be applied easily to the more general case.

Once the above process has been performed, the multiple point clouds are each in the coordinate space of the digitizer. Assume now that the origin of the digitizer coordinate space is at the center of the digitizer. These multiple point clouds sets typically cannot be superimposed (because they are not in the same coordinate space), so preferably a next step in the process is to transform them so that they are all in the same coordinate space. Any coordinate system may be used. For convenience, one may set the coordinate system of the first position to be a chosen global coordinate system, although this is not a limitation. Equivalently, it may be desirably to determine 4×4 matrices $T_M$ for each position M where $M \neq 1$, so that the matrix $T_M$ transforms the set $C_M$ into the coordinate space of the first set $C_1$. In particular, the following algorithm may be used to determine these matrices:

1. Set $T_1$ equal to the identity matrix.
2. for each i=2, . . . , N
   a. Perform a Iterative Closest Pair (ICP) alignment between $C_i$ and $C_{i-1}$ to determine a matrix Q such that Q transforms set $C_i$ into the same coordinate space as set $C_{i-1}$.
   b. Set $T_i = QT_{i-1}$ Once this process has been completed, the location of the digitizer at each position may now be computed as $O_i = T_i^{-1} (0, 0, 0)^T$ for each I=1, . . . , m.

For each position M (where M goes from 1 through N), as part of the 3D computation, one may determine a function $$F_M(x,y,z) \rightarrow (a,b),$$

where (x, y, z) is a real world 3D coordinate, and (a, b) is a pixel coordinate. Thus, for each position, a 3D coordinate may be mapped back to a corresponding pixel location on the image sensor. An example of such a function is the standard pinhole camera model, which may be applied to the imaging system using a standard lens calibration procedure to determine the image center (cx, cy) and focal length α:

$$F_M(x,y,z) = (cx + \alpha x/z, cy + \alpha y/z)$$

Processing of Images Using Photogrammetry

The next step is to process the full (or substantially full) illumination images $I_M$ using photogrammetry, and the known positions $O_M$. Each $I_M$ is composed of an array of pixels $S_M = \{(a_i, b_j) \, i=1 \ldots p, j=1 \ldots q\}$, where each pixel (p, q) may be considered to have an associated number value, and where the image sensor is assumed to have a resolution of p pixels in the horizontal direction, and q pixels in the vertical direction. This set may be reduced by noting that useful points on the object typically will only be near the coordinates contained in $C_M$. Consequently, for each position M, in one embodiment, this step marks every image point in $S_M$ as non-valid, and then determines which points are in fact valid. In particular, for each point (x, y, z) in $C_M$, compute the corresponding pixel coordinate (p, q) using $F_M$. Every pixel location within a certain neighborhood of (p, q) is then marked as valid. For example, if one chooses a neighborhood of 5 pixels, then every pixel with a distance of less than 5 pixels of (p, q) is marked as valid. Once this process has been completed, preferably all non-valid pixel pairs in $S_M$ are discarded.

Matching pixels between different positions (i.e., for different values of M) are then determined. This can be done by examining each pixel in the set $S_M$, and finding corresponding pixels in another set $S_Q$ where $M \neq Q$. There may be more than one set with a matching pixel. Well-known photogrammetry operations, such as cross-correlation, may be used to determine matching pixels. To aid in the search process, the system may take advantage of the fact that each pixel in $S_M$ also corresponds to a 3D coordinate in $C_M$, and that $F_M$ may be applied to that coordinate to obtain an initial guess for a neighborhood in $S_M$ for searching. For example, if (a, b) is a pixel in $S_M$, a corresponding 3D coordinate (x, y, z) is related to the pixel. $F_Q(x, y, z) = (c, d)$ produces a new pixel for position Q. For all subsequent searches in $S_Q$ to determine correspondence, the computations may then be restricted to a neighborhood of (c, d), thus significantly reducing the computational load for determining correspondence.

An additional performance improvement may be obtained by determining an epipolar line on the image for position Q, and searching along that portion of the epipolar line contained in the search neighborhood determined above. The epipolar geometry may be determined, for example, from intrinsic parameters for the camera, as well as from the extrinsic parameters obtained from the relevant alignment matrices $T_i$. The article "Multiple View Geometry in Computer Vision" by Richard Hartley and Andrew Zisserman, Second Edition, provides a detailed description of how to determine the epipolar line. This approach (incorporated by reference) allows a further improvement in the search for matching of features to occur in O(n) time as compared to $O(n^2)$ time.

Once the correspondence has been determined for all pixels, for any pixel that is found to correspond to at least one other pixel from another view, the next step is to form a bundle of rays from the origin of the camera to the pixel coordinate, with a ray for each corresponding pixel. A ray may be determined as a vector from the origin of the camera system through the pixel in question, and it may be determined from the camera model. Each bundle of rays is then converted into a 3D coordinate by intersecting the rays. If the rays do not intersect, a point of closest approach is chosen as long as that closest approach is within some maximum tolerance. The set of the 3D coordinates then forms the point cloud for the object.

Note that in the case where there are two sensors only, it may be desirable to only intersect rays from the images and point clouds associated with the two image sensors. In this way, the full process described above may be used with only one position of the digitizer.

When used for real-time capturing of data in the case of a two camera system, the improved 3D data (as computed using the methods above) may also be used for subsequent frames of images. Because of the high frame rate, the difference in digitizer location in space will be relatively small between subsequent captures. This allows for the 3D data from one or more previous capture(s) to be used as a starting point for the matching algorithm. After the matching has been computed, the 3D data is then computed and aligned to the existing 3D data as described above, and it may then be used as a starting point for the next set of images.

Alternative Method

An alternative method may be used when a two camera system is employed. In this case, a dense laser pattern is projected onto the object to be digitized. Two images are obtained from two different positions, simultaneously. In this case, the denser the laser pattern, the better. The laser also has the effect of producing a laser speckle pattern, such that, in addition to the intended illuminated pattern on the object, other blobs of reflected light are visible. In the case of a two camera system where the two images are taken simultaneously, this laser speckle pattern has the added benefit of providing additional feature points on the surface that are now imaged from two cameras. These feature points may be used in a standard photogrammetry analysis between the two images to perform the computation using a known (and calibrated) distance between the two camera sensors to obtain the 3D coordinates. Knowledge of how the laser speckle pattern behaves on the material is question also may be used to adjust the measured speckle feature points prior to doing the photogrammetric computation.

Figure 5:
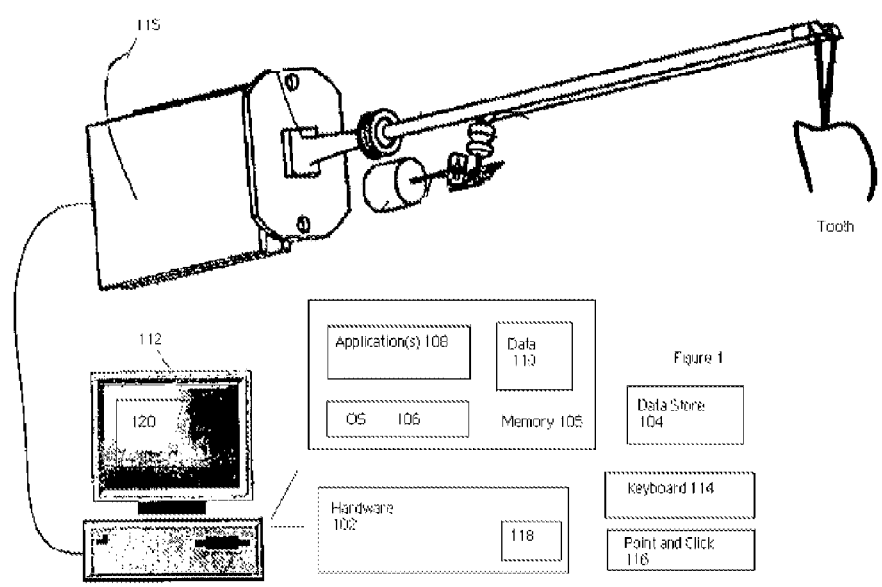
FIG. 5 is a dental system in which the 3D photogrammetry technique of this disclosure may be implemented.

The 3D photogrammetry computations described above (for any of the embodiments) may be implemented in a computer program, as a set of program instructions, executable in one or more processors. A representative computer is shown in FIG. 5 and comprises hardware 102, suitable storage 104 and memory 105 for storing an operating system 106, one or more software applications 108 and data 110, conventional input and output devices (a display 112, a keyboard 114, a point-and-click device 116, and the like), other devices 118 to provide network connectivity, and the like. A laser digitizer system 115 is used to obtain optical scans from a dental item, such as a patient's dental anatomy, as described above. Using a conventional graphical user interface 120, an operator can view and manipulate models as they are rendered on the display 112.

As described in an embodiment of U.S. Pat. No. 7,184,150, an intra-oral laser digitizer comprises a number of components, namely, a light source having collimating optics configured to generate a collimated beam of light, a scanner optically coupled to the light source and configured to scan the collimated beam along at least two axes, and a first optics relay coupled to the scanner and configured to relay the scanned collimated beam of light towards a remote object to be imaged. Over a given scanning period the scanned collimated beam of light generates a pattern comprising a set of segments. In particular, the pattern typically comprises a plurality of curves, with each curve being substantially parallel to one another. The digitizer typically also includes an image sensor, a reflecting surface configured to capture a reflection of the scanned collimated beam from the object at a given triangulation angle, and a second optics relay, co-linear to the first optics relay, where in the second optics relay is coupled to the reflecting surface and configured to relay the reflection of the scanned collimated beam toward the image sensor. Over the given scanning period the reflection of the scanned collimated beam on the image sensor comprises a modified pattern. A processor then uses the modified pattern, together with at least one other modified pattern generated as a result of scanning the collimated beam of light in a second pattern, to generate a representation of the remote object.

Figure 6:
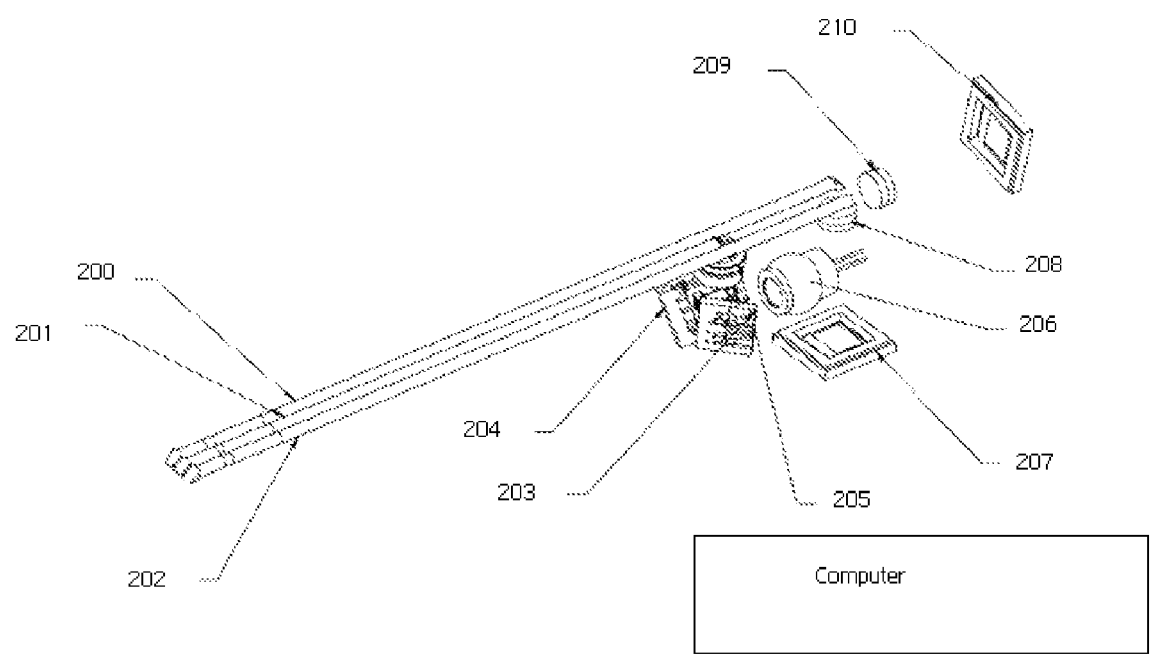
FIG. 6 is an exploded view of an intra-oral digitizer that includes a projection portion and a pair of imaging portions for use in the present invention.

FIG. 6 illustrates an exploded view of an intra-oral embodiment of a laser digitizer that corresponds to the embodiment of FIG. 2. This apparatus comprises a number of components: a first optical relay lens system 200 for imaging, an optical relay lens system 201 for projection, a second optical relay lens system 202 for imaging, a first scanning mirror 203, a second scanning mirror 204, a projecting coupling lens system 205, a laser or other light source system 206, a first imaging sensor 207, a first imaging focusing lens system 208, a second imaging focusing lens system 209, and a second imaging sensor 210. Components 201, 203-205 and 206 correspond generally to reference numeral P in FIG. 2. Components 200, 207, and 208 correspond generally to reference numeral I in FIG. 2; components 202, 209 and 210 correspond generally to reference numeral J in FIG. 2. In operation, the light from the laser source 206 is reflected off the high speed (x) mirror 203, and in turn reflected off the low speed (y) mirror 204, and focused through a lens assembly 205 onto a prism connected to a grin relay lens 201 and projected onto the object being scanned. Over a time interval (1/60 second, for example, or within one frame interval of a camera), the light forms a pattern on the object being scanned. The reflection of the pattern on the object is received through a right grin relay lens 200 and a left grin relay lens 202. The reflected light through the left relay lens 202 is focused through lens assembly 209 onto a first imaging sensor 210. The reflected light through the right relay lens 200 is deflected by a prism on the end of the relay lens and focused through a lens assembly 208 onto a second imaging sensor 207. The result is a left image from the sensor 210 and a right image from the sensor 207 of the projected pattern. These simultaneous left and right images, combined with knowledge of the projected pattern, are fed into the algorithms to compute the 3D data as described.

The above-described technique may be associated with a system that is used to design restorative models for permanent placement in a patient's mouth. As has been described, in a representative embodiment, a computer workstation in which the invention is implemented comprises hardware, suitable storage and memory for storing an operating system, one or more software applications and data, conventional input and output devices (a display, a keyboard, a point-and-click device, and the like), other devices to provide network connectivity, and the like. An intra-oral digitizer wand is associated with the workstation to obtain optical scans from a patient's anatomy. The digitizer scans the restoration site with a scanning laser system and delivers images to a monitor on the workstation. Although not shown, a milling apparatus may be associated with the workstation to mill a dental blank in accordance with a tooth restoration model created by the workstation.

While certain aspects or features of the present invention have been described in the context of a computer-based method or process, this is not a limitation of the invention. Moreover, such computer-based methods may be implemented in an apparatus or system for performing the described operations, or as an adjunct to other dental restoration equipment, devices or systems. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including optical disks, CD-ROMs, and magnetic-optical disks, read-only memories (ROMs), random access memories (RAMs), magnetic or optical cards, or any type of media suitable for storing electronic instructions, and each coupled to a computer system bus. The described functionality may also be implemented in firmware, in an ASIC, or in any other known or developed processor-controlled device.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic. Further, while given components of the system have been described separately, one of ordinary skill will appreciate that some of the functions may be combined or shared in given systems, machines, devices, processes, instructions, program sequences, code portions, and the like.

While given components of the system have been described separately, one of ordinary skill will appreciate that some of the functions may be combined or shared in given instructions, program sequences, code portions, and the like.

Having described our invention, what we now claim is as follows:

The invention claimed is:

1. A method for obtaining a 3D model of an object, comprising:
    projecting a pattern onto the object from at least first and second positions;
    observing the pattern from the first and second positions by capturing an image P of the pattern incident on the object;
    capturing an illumination image I of the object from each of the first and second positions, wherein the image I is captured using an imaging system comprising a projection portion and one or more imaging portions;
    forming a 3D model of the object for each of the first and second positions by analyzing observed distortions to the pattern P caused by a 3D surface of the object;
    using the 3D model in conjunction with each illumination image I to find a pixel in the illumination image I of the object from the first position that corresponds to a pixel in the illumination image I of the object from the second position, wherein the corresponding pixels are a matched pixel; and
    using photogrammetry to determine 3D coordinates for each matched pixel.

2. The method as described in claim 1 wherein the object is a dental item.

3. The method as described in claim 1 wherein the illumination image I is a full illumination image.

4. A non-transitory computer-readable medium having computer-executable instructions for performing the method steps of claim 1.

5. Apparatus comprising:
    an imaging system comprising a projection portion and one or more imaging portions, a processor in communication with the imaging system, and
    a computer-readable medium, the computer-readable medium having processor-executable instructions for performing the method steps of claim 1.

6. A method for obtaining a 3D model of an object, comprising:
    projecting a pattern onto the object from at least two positions;
    observing the pattern from those positions by capturing at least two images $P_1$ and $P_2$ from slightly different offset locations of the pattern incident on the object;
    capturing illumination images $I_1$ and $I_2$ of the object for each of the at least two positions, wherein the images $I_1$ and $I_2$ are captured using an imaging system comprising a projection portion and one or more imaging portions;
    forming a 3D model of the object for each position by analyzing observed distortions to the pattern P caused by the 3D surface of the object;
    using the 3D model in conjunction with each image $I_1$ and $I_2$ to find corresponding pixels between image $I_1$ and $I_2$; and
    using photogrammetry to determine 3D coordinates for each matched pixel.

7. The method as described in claim 6 wherein the object is a dental item.

8. The method as described in claim 5 wherein the illumination image is a full illumination image.

9. A method for obtaining a 3D model of an object, comprising:
    projecting a dense laser pattern onto the object;
        observing the dense laser pattern and any associated speckle from the position by capturing at least two images $P_1$ and $P_2$ from different offset locations of the laser pattern incident on the object, wherein the at least two images $P_1$ and $P_7$ are captured using an imaging system comprising a projection portion and one or more imaging portions;
        matching equivalent pairs of speckle features between the two images; and
        using photogrammetry to determine 3D coordinates for each matched pixel.

10. A non-transitory computer-readable medium having computer-executable instructions for performing the method steps of claim 9.

11. Apparatus comprising:
    an imaging system comprising a projection portion and one or more imaging portions,
    a processor in communication with the imaging system, and
    a computer-readable medium, the computer-readable medium having processor-executable instructions for performing the method steps of claim 9.

12. An imaging system, comprising:
    an intra-oral digitizer, comprising:
        a light source having collimating optics configured to generate a collimated beam of light;
        a scanner optically coupled to the light source and configured to scan the collimated beam along at least two axes;
        a first optics relay coupled to the scanner and configured to relay the scanned collimated beam of light towards a dental object to be imaged, wherein over a given scanning period the scanned collimated beam of light generates a pattern comprising a set of segments;

a first image sensor;

a second image sensor;

a second optics relay, co-linear to the first optics relay, configured to relay a reflection of the scanned collimated beam toward the first image sensor, wherein over the given scanning period the reflection of the scanned collimated beam on the first image sensor comprises a first modified pattern; and a third optics relay, co-linear to the first optics relay, configured to relay a reflection of the scanned collimated beam toward the second image sensor, wherein over the given scanning period the reflection of the scanned collimated beam on the first image sensor comprises a second modified pattern; and a computer coupled to the intra-oral digitizer that (a) uses at least the first and second modified patterns to generate a 3D model of a surface of the dental object, (b) uses the 3D model in conjunction with at least first and second images of the dental object to find matching pixels between the first and second images, and (c) uses photogrammetry to determine 3D coordinates for each matched pixel.

* * * * *